(12) United States Patent
Kryzhanovskii et al.

(10) Patent No.: US 10,932,702 B2
(45) Date of Patent: Mar. 2, 2021

(54) METHOD FOR NONINVASIVELY DETERMINING BLOOD GLUCOSE CONCENTRATION

(71) Applicants: Edvard Vladimirovich Kryzhanovskii, Saint-Petersburg (RU); Artem Sergeevich Adzhemov, Moscow (RU); Armen Gareginovich Grigoryan, Saint-Petersburg (RU)

(72) Inventors: Edvard Vladimirovich Kryzhanovskii, Saint-Petersburg (RU); Artem Sergeevich Adzhemov, Moscow (RU); Armen Gareginovich Grigoryan, Saint-Petersburg (RU)

( * ) Notice: Subject to any disclaimer, the term of this patent is extended or adjusted under 35 U.S.C. 154(b) by 695 days.

(21) Appl. No.: 15/538,840

(22) PCT Filed: Dec. 17, 2015

(86) PCT No.: PCT/RU2015/000891
§ 371 (c)(1),
(2) Date: Dec. 7, 2017

(87) PCT Pub. No.: WO2016/105248
PCT Pub. Date: Jun. 30, 2016

(65) Prior Publication Data
US 2018/0146893 A1    May 31, 2018

(30) Foreign Application Priority Data

Dec. 22, 2014   (RU) ............................ RU2014152166

(51) Int. Cl.
*A61B 5/1455*    (2006.01)
*A61B 5/00*      (2006.01)
*A61B 5/145*     (2006.01)

(52) U.S. Cl.
CPC .......... *A61B 5/1455* (2013.01); *A61B 5/0075* (2013.01); *A61B 5/14532* (2013.01);
(Continued)

(58) Field of Classification Search
None
See application file for complete search history.

(56) References Cited

U.S. PATENT DOCUMENTS 6,167,290 A * 12/2000 Yang ................. A61B 5/14532
600/316

* cited by examiner

*Primary Examiner* — Marjan Fardanesh
(74) *Attorney, Agent, or Firm* — The Weintraub Group, P.L.C.

(57) ABSTRACT

A method for noninvasive determination of glucose content in blood. The method includes optically irradiating a biomaterial alternately in any sequence with optical radiation of a first wavelength band of 950-970 nm, optical radiation of a second wavelength band of 1020-1060 nm, optical radiation of a third wavelength band of 930-950 nm, optical radiation of a fourth wavelength band of 740-760 nm and optical radiation of a fifth wavelength band of 830-850 nm, receiving Ron with a receiver the optical radiation diffusely reflected by the biomaterial, converting the received optical radiation into an electric signal and determining the glucose concentration in blood on the basis of the sum of the electric signals received at radiation treatment of the biomaterial with the optical radiation of the second, third and fourth bands which is reduced by values determined by the electric signal received at radiation treatment of the biomaterial with optical radiation of the first and fourth bands. The invention ensures enhanced accuracy of determination of glucose concentration in blood due to reducing of the error of measurements caused by presence of water and melanin in the biomaterial under survey.

1 Claim, 2 Drawing Sheets

(52) U.S. Cl.
CPC .......... *A61B 5/7278* (2013.01); *A61B 5/7203* (2013.01); *A61B 2560/0223* (2013.01)

METHOD FOR NONINVASIVELY DETERMINING BLOOD GLUCOSE CONCENTRATION

BACKGROUND OF THE INVENTION

1. Field of the Invention

The invention relates to the field of survey and analysis of materials chemical composition and can be preferentially used in diagnostic medical equipment for non-invasive determination of glucose content in blood.

2. Prior Art

A method of noninvasive measuring of a substance concentration in a human body, e.g. glucose concentration in the human's blood, is known (RU 2511405 C2, 2014), in realization whereof a value of infrared radiation emitted and/or dissipated by a human body with the wavelength range 8.5-10.5 μm, which includes at least one glucose characterizing wavelength, shall be determined; the temperature of a detector and of one or more components of the optical system shall be measured, and the temperature of the detector and of one or more components of the optical system shall be compared with a set of pre-set calibrating parameters for correction of the detected value of infrared radiation taking into account the impact of radiation of each detector and one or more components of the optical system.

As noted by the authors of this invention, the choice of the far infrared wavelength band as a working range was conditioned by the fact that glucose possesses expressed and well-discerned absorbance spectra in the mentioned band, which, unlike technical solutions wherein the near infrared wavelength band is conventionally used, allows producing a larger valid signal value but requires cryogenic cooling of the equipment which results in significant complicating of the device for realization of the method and increasing of its overall dimensions.

The authors of this known method managed to put aside the use of cryogenic cooling, when realizing the known method, by correcting results of measuring of the valid signal on basis of results of temperature measuring of the human body and environment, plus by temperature measuring of optical radiation and that of all components of the device's optical system, which also leads to significant complicating of the design of the mentioned device.

Among methods wherein optical radiation of the near infrared and/or visible wavelength band is used, which do not require cooling or measuring and consideration of temperature, known are, for instance, the method of noninvasive measuring of glucose concentration in blood (RU 2515410 C2, 2014) and the method allowing application of the known diode laser device for noninvasive measuring of glycemia (RU 2468356 C2, 2012) which in their common part include radiation of a biomaterial with a laser's optical radiation, conversion of the optical radiation, reflected and dissipated with the biomaterial, into an electric signal and calculation of the glucose concentration in blood on basis of the amplitude value of this electric signal, whereas monochromatic optical radiation is used with wavelength 650 nm (RU 2515410 C2, 2014) or visible and infrared optical radiation within the wavelength range from 500 nm to 1100 nm.

The closest to the claimed method of noninvasive determination of glucose concentration in blood in its technical substance is the known method of noninvasive measuring of glucose concentration in blood (RU 2122208 C1, 1998) which provides radiation of blood vessels with collimated optical radiation of a semi-conductor laser with the varied wavelength within 1.3 to 1.9 μm at a gradual increase of the current applied thereon and constant regulation of temperature, registration of the radiation which is absorbed, dissipated and diffusely-reflected with the blood by conversion thereof into an electric signal ad thereafter into a numerical code with a calibration curve and determination, via the result of comparison, of a value of glucose concentration with further reproduction of the value on a digital screen.

A drawback both of the closest analogue and all other analogues considered above is insufficient accuracy of determination of glucose concentration in blood which is related to the error of measurements caused by the significant percentage of water and melanin in a biomaterial under survey, while water and melanin have expressed and discerned spectra of optical radiation absorbance spectra within the wavelength bands used in the considered analogues.

SUMMARY OF THE INVENTION

The objective of this invention was creation of a method of noninvasive determination of glucose concentration in blood which would provide achieving of a technical result constituting in enhanced accuracy of determination of glucose concentration in blood.

The set objective has been solved, according to this invention, owing to that the method of noninvasive determination of glucose concentration in blood, including, in accordance with the closest analogue, radiation treatment of a biomaterial with optical radiation of a near infrared wavelength band, receiving of the optical radiation diffusely-reflected with the biomaterial, conversion of the received optical radiation into an electric signal and determination of glucose concentration in blood on basis of the received electric signal, differs from the closest analogue by that the radiation treatment of the biomaterial is performed alternately in any sequence with the first band optical radiation of wavelengths 950-970 nm, the second band optical radiation of wavelengths 1020-1060 nm and the third band optical radiation of wavelengths 930-950 nm, while determination of glucose concentration in blood is performed on basis of a value of the sum of the electric signals received at radiation of the biomaterial with the second and third band optical radiation which is decreased by a value determined by the electric signal received at radiation of the biomaterial with the first band optical radiation.

At a better realization of the invention, a biomaterial is additionally treated with radiation with the fourth band optical radiation of wavelength 740-760 nm, while determination of glucose concentration in blood is realized on basis of the sum of electric signals received at radiation of the biomaterial with the second and third band optical radiation which is decreased by values determined by the electric signals received at radiation of the biomaterial with the first and fourth bands optical radiation.

At a better realization of the invention, a biomaterial is additionally treated with the fifth band optical radiation of wavelength 830-850 nm, while determination of glucose concentration in blood is realized on basis of the sum of electric signals received at radiation of the biomaterial with the second, third and fifth band optical radiation which is decreased by values determined by the electric signals received at radiation of the biomaterial with the first band optical radiation.

At the best realization of the invention, a biomaterial is additionally radiated with the fourth band optical radiation of wavelength 740-760 nm, while determination of glucose concentration in blood is realized on basis of the sum of electric signals received at radiation of the biomaterial with the second, third and fifth band optical radiation which is decreased by values determined by the electric signals received at radiation of the biomaterial with the first and fourth bands optical radiation.

Whereas, determination of glucose concentration in blood is realized with use of the experimentally derived calibration dependence between the glucose concentration and the received aggregate electric signal having the value $U_{SUM}=U_2+U_3+U_5-U_1(\kappa_{12}+\kappa_{13}+\kappa_{15})-U_4(\kappa_{42}+\kappa_{43}+\kappa_{45})$, where $U_1$, $U_2$, $U_3$, $U_4$, $U_5$ are values of the electric signals received at radiation treatment of the biomaterial with the first, second, third, fourth and fifth bands of optical radiation, respectively; $\kappa_{12}$, $\kappa_{13}$, $\kappa_{15}$ are the factors pre-received on basis of combined processing of the known characteristics of relative spectral responsivity of the applied receiver and the water absorbance spectrum in the first, second, third and fifth wavelength bands, respectively; $\kappa_{42}$, $\kappa_{43}$, $\kappa_{45}$ are the factors pre-received on basis of combined processing of the known characteristics of relative spectral responsivity of the used receiver of the optical radiation and the melanin absorbance spectrum in the second, third, fourth and fifth wavelength bands, respectively.

The factors at the combined processing of known characteristics of the relative spectral responsivity of the applied optical radiation receiver and the water absorbance spectrum in the first, second, third and fifth wavelength bands are pre-determined by the formulas $\kappa_{12}=K_2S_2/K_1/S_1$, $\kappa_{13}=K_3S_3/K_1/S_1$, $\kappa_{15}=K_5S_5/K_1/S_1$, where $K_1$, $K_2$, $K_3$, $K_5$ are average values of water absorbance factors in the first, second, third and fifth wavelength bands, respectively; $S_1$, $S_2$, $S_3$, $S_5$ are average values of relative spectral responsivity of the applied optical radiation receiver in the first, second, third and fifth wavelength bands, respectively.

The factors at combined processing of known characteristics of the relative spectral responsivity of the applied optical radiation receiver and the water absorbance spectrum in the second, third, fourth and fifth wavelength bands are pre-determined in accordance with formulas $\kappa_{42}=K_2S_2/K_4/S_4$, $\kappa_{43}=K_3S_3/K_4/S_4$, $\kappa_{45}=K_5S_5/K_4/S_4$, where $K_2$, $K_3$, $K_4$, $K_5$ are average values of melanin absorbance factors in the second, third, fourth and fifth wavelength bands, respectively; $S_2$, $S_3$, $S_4$, $S_5$ are average values of relative spectral responsivity of the applied optical radiation receiver in the second, third, fourth and fifth wavelength bands, respectively.

It is known that the absorbance spectrum of glucose optic radiation in the near infrared band of wavelengths from 800 nm to 1100 nm possesses expressed and discerned maximums near wavelengths of 1040 nm, 940 nm and 840 nm (here the wavelengths are given in decreasing order of the maximum values corresponding thereto). So the use, in the claimed method, of radiation treatment of a biomaterial with the second band optical radiation of wavelength 1020-1060 nm and the third band optical radiation of wavelength 930-950 nm, and with the fifth band optical radiation of wavelength 830-850 nm at the better realization of the method allows to receive at implementation thereof a larger valid signal value.

At the same time, biomaterials contain significant amounts of water and melanin.

Water possesses the most expressed absorbance spectrum in wavelength band from 800 nm to 1100 nm with the maximum near the wavelength of 960 nm, the value whereof even exceeds the value of the utmost maximum of glucose absorbance spectrum located near the wavelength of 1040 nm. So the presence of water leads to distortion of the valid signal which is manifested in an increase of the electric signal due to absorbance of optical radiation of the second, third and fifth wavelength bands by water, and at the same time contributes to the most significant measurement error at determining of glucose concentration.

The absorbance spectrum of melanin optical radiation within wavelength bands from 700 nm to 1100 nm does not possess maximums but is of a quite uniform nature, but its value even exceeds the maximum value of glucose absorbance spectrum near the wavelength of 840 nm, which results in distortion of the valid signal conditioned with absorbance of optical radiation of the fifth wavelength band by glucose by more than 100%. Presence of melanin in the biomaterial under study, also due to the distortion, shall lead to increase of the valid signal which is conditioned by absorbance of optical radiation of the second and third wavelength bands by glucose by 30-40%. Thus, presence of melanin in the biomaterial under study at a certain glucose concentration with use of radiation treatment of the biomaterial by optical radiation of the second, third and fifth wavelength bands shall lead to occurrence of a measurement error which is less than that caused by water, but being still quite significant.

To evaluate and account for the measurement error caused by presence of water in the biomaterial under study in accordance with this invention, the authors propose that prior, after or between the second band optical radiation treatment with wavelengths of 1020-1060 nm and the third band optical radiation treatment with wavelengths of 930-950 nm which provides for producing of valid signal for determination of glucose determination, it is needed to perform radiation treatment of the biomaterial by the first band optical radiation with wavelengths of 950-970 nm wherein the maximum of water absorbance spectrum is located, and as a result of receiving of the first wavelength optical radiation diffusely-reflected with the biomaterial, to receive an electric signal which is determined mostly by a current value of water concentration in the biomaterial under study. So, determination of glucose concentration in blood on basis of the sum of electric signals received at radiation treatment of the biomaterial by the second and third bands optical radiation (wherein two utmost maximums of glucose absorbance spectrum are located) which is decreased by the value determined by the electric signal received at radiation treatment of the biomaterial with the first wavelength optical radiation (wherein a maximum of water absorbance spectrum is located) allows accounting for an error conditioned by presence of water in the biomaterial under study and thus increasing accuracy of glucose concentration determination.

At the better realization of the invention, in purpose of enhancing the accuracy of glucose concentration determination due to accounting of the error caused by presence of melanin in the biomaterial under study, the biomaterial is additionally treated only with the fourth band optical radiation with wavelengths of 740-760 nm wherein absorbance of optical radiation with glucose and water is practically absent, and as a result of accepting the diffusely-reflected optical radiation of the fourth wavelength band the electric signal is received which is determined by the current value of melanin concentration in the biomaterial under study. So, determination of glucose concentration in blood on basis of the sum of electric signals received at radiation treatment with the second and third band optical radiation (wherein two utmost maximums of glucose absorbance spectrum are located) which is decreased by the values determined by the electric signals received at radiation treatment of the biomaterial with the first wavelength band optical radiation (wherein a maximum of water absorbance spectrum is located) and the fourth band (whereby melanin concentration is evaluated) allows accounting for errors conditioned by presence of both water and melanin in the biomaterial under study and thus increasing accuracy of glucose concentration determination.

At the best realization of the invention, in purpose of enhancing the accuracy of glucose concentration determination the biomaterial is radiation treated alternately in any sequence not only with the first band optical radiation, second band optical radiation, third band optical radiation and fourth band optical radiation, but also with the fifth band optical radiation with the wavelength 830-850 nm (wherein the third smallest maximum of glucose absorbance spectrum is located), while determination of glucose concentration in blood is performed on basis of the sum of electric signals received at radiation treatment of the biomaterial by optical radiation of the second, third and fifth band (wherein all three maximums of glucose absorbance spectrum are located) which is decreased by the values determined by electric signals received at radiation treatment of the biomaterial by optical radiation of the first band (wherein the maximum of water absorbance spectrum is located) and of the fourth band (whereon melanin concentration is evaluated).

The above mentioned speaks for solving of the task of this invention declared herein above thanks to availability of the above mentioned characteristic features of the claimed method of noninvasive determination of glucose concentration in blood.

BRIEF DESCRIPTION OF THE DRAWING

Shown in FIG. 1 is the structural scheme of the device which allows in the best way to realize the claimed method of noninvasive determination of glucose concentration in blood where 1—LED unit, 2—optical radiation receiver, 3—amplifier, 4—AD converter, 5—controller, 6—indication unit, and 7—biomaterial.

Shown in FIG. 2 are spectrums of absorbance of optical radiation of glucose, water and melanin in the wavelength band from 700 nm to 1150 nm, where the first, second, third, fourth and fifth bands of optical radiation wavelength are shown with Roman figures I, II, III, IV and V, respectively.

DETAILED DESCRIPTION OF THE INVENTION

Figure 1:
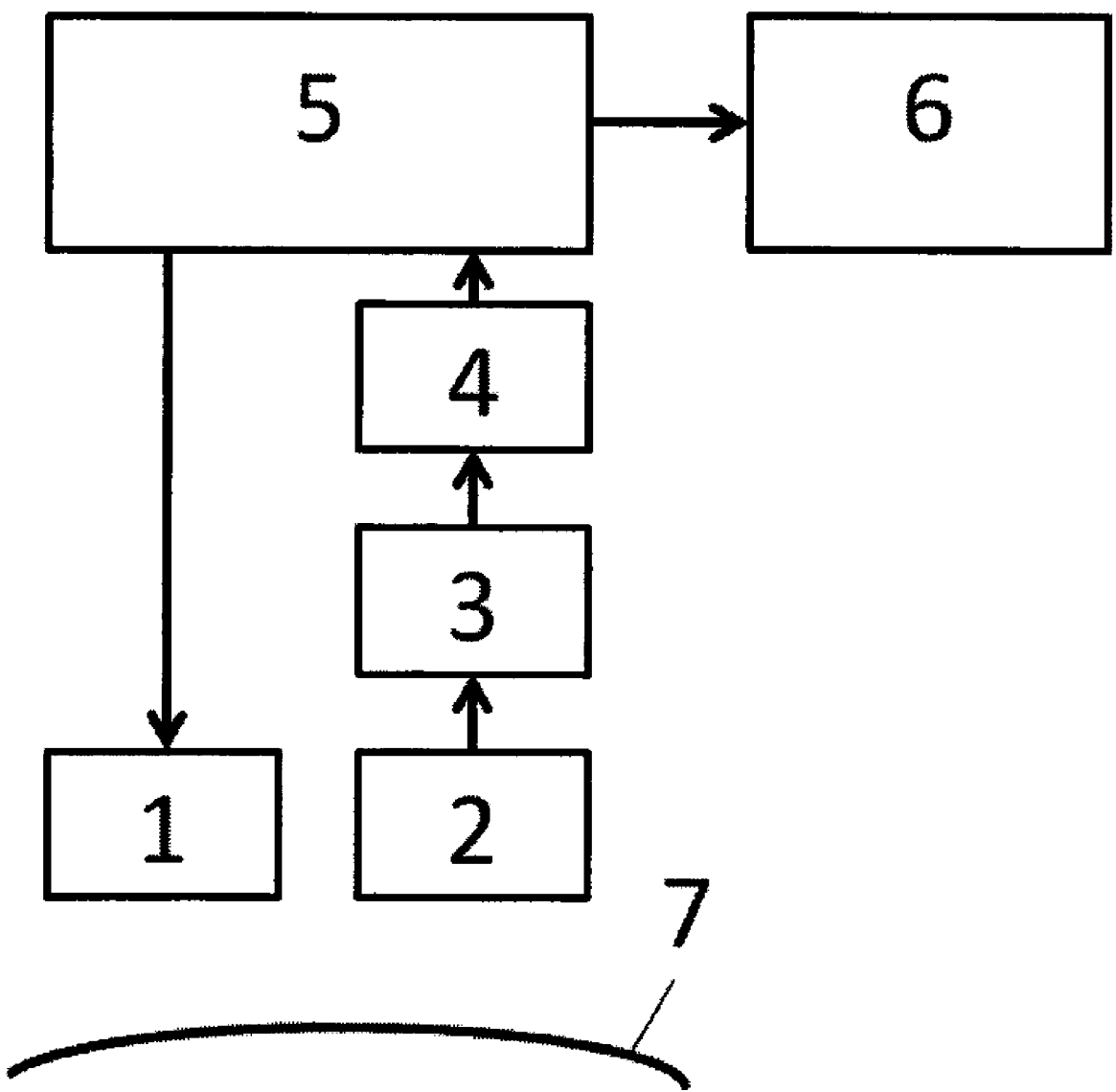

A device which allows to realize, in the best way, the claimed method of noninvasive determination of glucose concentration in blood contains consequently connected receiver 2 of optical radiation, amplifier 3, AD converter 4, controller 5 and indication unit 6, and also LED unit 1 connected to the output of controller 5.

LED unit 1 contains at least one LED performed with possibility to emit optical radiation in the first band of wavelength 950-970 nm, e.g. of SIM-012ST type; at least one LED performed with possibility to emit optical radiation in the second band of wavelength 1020-1060 nm, e.g. of OIS-150-1020 type; at least one LED performed with possibility to emit optical radiation in the third band of wavelength 930-950 nm, e.g. of KM2520F3C03 type; at least one LED performed with possibility to emit optical radiation in the fourth band of wavelength 740-760 nm, e.g. of EDEF-1LS3 type; and at least one LED performed with possibility to emit optical radiation in the fifth band of wavelength 830-850 nm, e.g. of EDEI-1LS3 type.

As receiver 2 of optical radiation, a photo diode is used which is sensitive to optical radiation in the band of wavelength from 740 nm to 1060 nm, e.g. photo diode of BPW34 type.

Receiver 2 of optical radiation and LEDs of LED unit 1 are installed on a common base (not shown in FIG. 1) which is made with possibility of being pressed to a biomaterial 7 under study, whereas LEDs are located around receiver 2 of optical radiation.

As amplifier 3, a precision operation amplifier is used, e.g. of AD8604 type.

As AD converter 4, an analogue-digital converter AD7655 is used.

As controller 5, microcontroller ATXmega128A4U is used which is equipped with ROM (read-only memory) and RAM (random access memory).

The device which allows in the best way to realize the claimed method of noninvasive determination of glucose concentration in blood shall operate as follows.

To determine glucose concentration in blood, the base with receiver 2 of optical radiation and LEDs of LED unit 1 are pressed to the biomaterial 7 under study.

After the device is on, LEDs of LED unit 1 do not emit optical radiation. The electric signal from receiver 2 of optical radiation determined by its dark current is amplified with amplifier 3 and converted with AD converter 4 into a digital code which is delivered to controller 5 and saved in its random access memory.

After that, on basis of signals from controller 5, voltage is alternately applied to LEDs of LED unit 1. To realize the claimed method, the sequence of switching of LEDs is immaterial.

Figure 2:
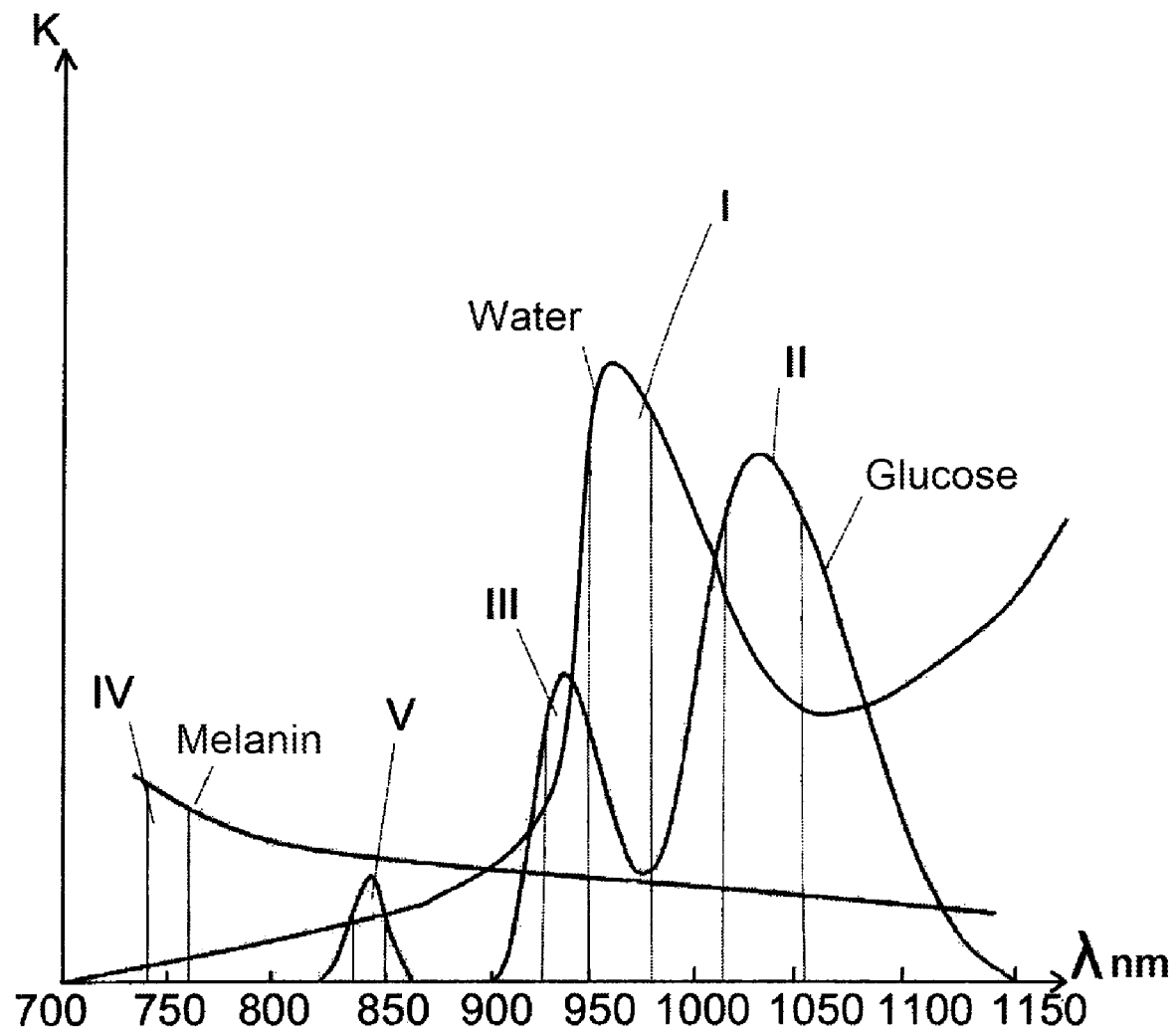

For example, in case of application of voltage to a LED of LED unit 1 which is made with possibility to emit optical radiation in the first band I with wavelength 950-970 nm (see FIG. 2); the latter emits optical radiation of the mentioned wavelength band towards the biomaterial 7 under study. A portion of the incident optical radiation is absorbed predominantly with water, while another portion is diffusely reflected and downfalls onto receiver 2 of optical radiation which converts this portion of optical radiation into an electric signal determined, to a larger extent, by concentration of water in the biomaterial 7 under study, and to a lesser extent by glucose and melanin. This electric signal is amplified with amplifier 3 and after conversion into the digital code with AD converter 4 is delivered to controller 5 which, in purpose of accounting for a measurement error conditioned by the dark current of receiver 2 of optical radiation, subtracts from this digital code the digital code which is saved in RAM and corresponds to the electric signal from the dark current of receiver 2 of optical radiation, and enters into the RAM the produced difference which corresponds to the electric signal $u_1$, the value whereof is determined predominantly by concentration of water in biomaterial 7 under study.

Thereafter the LED which was switched on earlier goes off, but as a result of voltage application, e.g. on a LED of LED unit 1 made with possibility to emit optical radiation in the fourth band IV (see FIG. 2) with wavelengths 740-760 nm, the latter emits optical radiation of the mentioned band towards the biomaterial 7 under study. Similarly, receiver 2 of optical radiation converts the diffusely reflected optical radiation into an electric signal which is determined by melanin concentration in biomaterial 7 under study, as there is practically no absorbance of optical radiation of this wavelength band by glucose and water. This electric signal is amplified with amplifier 3 and after being converted with AD converter 4 into the digital code is delivered to controller 5, in purpose of accounting for a measurement error conditioned by the dark current of receiver 2 of optical radiation, subtracts from this digital code the digital code which is saved in RAM and corresponds to the electric signal from the dark current of receiver 2 of optical radiation, and enters into the RAM the produced difference which corresponds to the electric signal $u_4$, the value whereof is determined predominantly by concentration of melanin in biomaterial 7 under study.

Thereafter the LED which was switched on earlier goes off, but as a result of voltage application, e.g. on a LED of LED unit 1 made with possibility to emit optical radiation in the second band II with wavelengths 1020-1060 nm (see FIG. 2), the latter emits optical radiation of the mentioned band towards the biomaterial 7 under study. Similarly, receiver 2 of optical radiation converts the diffusely reflected optical radiation into an electric signal which is determined not only by glucose concentration in biomaterial 7 under study, but also by water and melanin concentrations. This electric signal is amplified with amplifier 3 and after being converted with AD converter 4 into the digital code is delivered to controller 5, in purpose of accounting for a measurement error conditioned by the dark current of receiver 2 of optical radiation, subtracts from this digital code the digital code which is saved in RAM and corresponds to the electric signal from the dark current of receiver 2 of optical radiation, and enters into the RAM the produced difference which corresponds to the electric signal $u_2$, the value whereof is determined predominantly by concentration of glucose, water and melanin in biomaterial 7 under study.

Thereafter the LED which was switched on earlier goes off, but as a result of voltage application, e.g. on a LED of LED unit 1 made with possibility to emit optical radiation in the third band III with wavelengths 930-950 nm (see FIG. 2), the latter emits optical radiation of the mentioned band towards the biomaterial 7 under study. Similarly, receiver 2 of optical radiation converts the diffusely reflected optical radiation into an electric signal which is determined not only by glucose concentration in biomaterial 7 under study, but also by water and melanin concentrations. This electric signal is amplified with amplifier 3 and after being converted with AD converter 4 into the digital code is delivered to controller 5, in purpose of accounting for a measurement error conditioned by the dark current of receiver 2 of optical radiation, subtracts from this digital code the digital code which is saved in RAM and corresponds to the electric signal from the dark current of receiver 2 of optical radiation, and enters into the RAM the produced difference which corresponds to the electric signal $u_3$, the value whereof is determined predominantly by concentration of glucose, water and melanin in biomaterial 7 under study.

And finally, the LED which was switched on earlier goes off again, but as a result of voltage application, e.g. on a LED of LED unit 1 made with possibility to emit optical radiation in the fifth band V with wavelengths 830-850 nm (see FIG. 2), the latter emits optical radiation of the mentioned band towards the biomaterial 7 under study. Similarly, receiver 2 of optical radiation converts the diffusely reflected optical radiation into an electric signal which is determined not only by glucose concentration in biomaterial 7 under study, but also by water and melanin concentrations. This electric signal is amplified with amplifier 3 and after being converted with AD converter 4 into the digital code is delivered to controller 5, in purpose of accounting for a measurement error conditioned by the dark current of receiver 2 of optical radiation, subtracts from this digital code the digital code which is saved in RAM and corresponds to the electric signal from the dark current of receiver 2 of optical radiation, and enters into the RAM the produced difference which corresponds to the electric signal $u_5$, the value whereof is determined predominantly by concentration of glucose, water and melanin in biomaterial 7 under study.

Thereafter the contemplated processes of alternate switching, on basis of signals from controller 5, of LEDS of LED unit 1, conversion of the reflected optical radiation into the electric signal with receiver 2 of optical radiation and processing of the received digital codes with controller 5 are repeated multiple times. As a result, samples of values of electric signals $u_1$, $u_2$, $u_3$, $u_4$ and $u_5$ are accumulated in the RAM of controller 5, which are statistically processed with controller 5 for filtering of random errors; as a result, averaged values of electric signals $U_1$, $U_2$, $U_3$, $U_4$, and $U_5$ are formed, respectively, and saved in the RAM of controller 5.

On basis of the produced averaged values of electric signals, controller 5 calculates the value of the aggregate electric signal per the following expression:

$$U_{SUM}=U_2+U_3+U_5-U_1(\kappa_{12}+\kappa_{13}+\kappa_{15})-U_4(\kappa_{42}+\kappa_{43}+\kappa_{45}),$$

where $U_1$, $U_2$, $U_3$, $U_4$, $U_5$ are averaged values of electric signals received at radiation treatment of the biomaterial by optical radiation of the first, second, third, fourth and fifth bands, respectively;

$\kappa_{12}$, $\kappa_{13}$, $\kappa_{15}$ are factors preliminarily received on basis of joint processing of the known characteristics of relative spectral responsivity of the utilized receiver 2 of optical radiation and the spectrum of water absorbance in the first, second, third and fifth wavelength bands, respectively, and saved in the ROM of controller 5;

$\kappa_{42}$, $\kappa_{43}$, $\kappa_{45}$ are factors preliminarily received on basis of joint processing of the known characteristics of relative spectral responsivity of the utilized receiver 2 of optical radiation and the spectrum of melanin absorbance in the second, third, fourth and fifth wavelength bands, respectively, and saved in the ROM of controller 5.

In course of pre-processing of the known characteristics of relative spectral responsivity of the utilized receiver 2 of optical radiation and the spectrum of water absorbance in the first, second, third and fifth wavelength bands, the mentioned factors are determined per expressions $\kappa_{12}=K_2S_2/K_1S_1$, $\kappa_{13}=K_3S_3/K_1S_1$, $\kappa_{15}=K_5S_5/K_1S_1$, where $K_1$, $K_2$, $K_3$, $K_5$ are average values of water absorbance factors in the first, second, third and fifth wavelength bands, respectively; $S_1$, $S_2$, $S_3$, $S_5$ are average values of relative spectral responsivity of the utilized receiver 2 of optical radiation in the first, second, third and fifth wavelength bands, respectively.

In course of pre-processing of the known characteristics of relative spectral responsivity of the utilized receiver 2 of optical radiation and the spectrum of melanin absorbance in the second, third, fourth and fifth wavelength bands, the mentioned factors are determined per expressions $\kappa_{42}=K_2S_2/K_4S_4$, $\kappa_{43}=K_3S_3/K_4S_4$, $\kappa_{45}=K_5S_5/K_4S_4$, where $\kappa_2$, $\kappa_3$, $\kappa_4$, $\kappa_5$ are average values of melanin absorbance factors in the second, third, fourth and fifth wavelength bands, respectively; $S_2$, $S_3$, $S_4$, $S_5$ are average values of relative spectral responsivity of the utilized receiver 2 of optical radiation in the second, third, fourth and fifth wavelength bands, respectively.

Controller 5 determines the glucose concentration in blood on basis of the received value of the aggregate electric signal $U_{SUM}$ with use of the calibration dependence between the glucose concentration and the received aggregate electric signal $U_{SUM}$ which was prior experimentally received and recorded into the ROM of controller 5.

The received value of glucose concentration in blood from controller 5 is delivered to indication unit 6 which displays this value to an operator of the device.

The authors of this invention designed and tested an experimental model of the device which allows to embody in the best way the claimed method of noninvasive determination of glucose concentration in blood. Tests of the experimental model showed, first, its workability and, second, possibility to achieve the technical result which is expressed in enhanced accuracy of determination of glucose concentration in blood due to decrease by 28-34% of the measurement error conditioned by presence of water and melanin in the biomaterial under study.

What is claimed is:

1. A method for a noninvasive determination of glucose concentration in blood, including:
   (a) alternating irradiation of a biomaterial, in any sequence, with optical radiation in a first range, with wavelengths from 950 to 970 nm, optical radiation in a second range, with wavelengths from 1020 to 1060 nm, optical radiation in a third range, with wavelengths from 930 to 950 nm, optical radiation in a fourth range, with wavelengths from 740 to 760 nm, and optical radiation in a fifth range, with wavelengths from 830 to 850 nm;
   (b) receiving with an optical radiation receiver the optical radiation diffusely reflected by the biomaterial;
   (c) converting the received optical radiation into a resulting electrical signal; and
   (d) determining the glucose concentration in blood using the resulting electrical signal and an experimentally obtained calibration relationship between the glucose concentration and the resulting electrical signal, which has the value $U_{SUM}=U_2+U_3+U_5-U_1(\kappa_{12}+\kappa_{13}+\kappa_{15})-U_4(\kappa_{42}+\kappa_{43}+\kappa_{45})$, where $U_1$, $U_2$, $U_3$, $U_4$, and $U_5$ are each value of the resulting electrical signal obtained by irradiating the biomaterial with optical radiation of the first, second, third, fourth, and fifth ranges, respectively, $\kappa_{12}$, $\kappa_{13}$, $\kappa_{15}$, $\kappa_{42}$, $\kappa_{43}$, and $\kappa_{45}$ are factors preliminarily calculated according to the following expressions: $\kappa_{12}=K_{W2}S_2/K_{W1}/S_1$, $\kappa_{13}=K_{W3}S_3/K_{W1}/S_1$, $\kappa_{15}=K_{W5}S_5/K_{W1}/S_1$, $\kappa_{42}=K_{M2}S_2/K_{M4}/S_4$, $\kappa_{43}=K_{M3}S_3/K_{M4}/S_4$, $\kappa_{45}=K_{M5}S_5/K_{M4}/S_4$, where $K_{W1}$, $K_{W2}$, $K_{W3}$, and $K_{W5}$ are average values of the water absorption coefficients in the first, second, third, and fifth wavelength ranges, respectively, $K_{M2}$, $K_{M3}$, $K_{M4}$, and $K_{M5}$ are average values of melanin absorption coefficients in the second, third, fourth, and fifth wavelength ranges, respectively, $S_1$, $S_2$, $S_3$, $S_4$, and $S_5$ are average values of relative spectral sensitivities of the optical radiation receiver in the first, second, third, fourth, and fifth wavelength ranges, respectively.

* * * * *